(12) United States Patent  
Aelen et al.

(10) Patent No.: US 10,667,703 B2  
(45) Date of Patent: Jun. 2, 2020

(54) APPARATUS FOR TRACKING A SPECIFIC BLOOD PRESSURE

(71) Applicant: KONINKLIJKE PHILIPS N.V., Eindhoven (NL)

(72) Inventors: Paul Aelen, Eindhoven (NL); Pierre Hermanus Woerlee, Valkenswaard (NL); Wouter Herman Peeters, Waalre (NL); Simone Cornelia Maria Anna Ordelman, 's-Hertogenbosch (NL)

(73) Assignee: Koninklijke Philips N.V., Eindhoven (NL)

( * ) Notice: Subject to any disclaimer, the term of this patent is extended or adjusted under 35 U.S.C. 154(b) by 141 days.

(21) Appl. No.: 15/034,015

(22) PCT Filed: Mar. 3, 2014

(86) PCT No.: PCT/IB2014/059384  
§ 371 (c)(1),  
(2) Date: May 3, 2016

(87) PCT Pub. No.: WO2015/068053  
PCT Pub. Date: May 14, 2015

(65) Prior Publication Data  
US 2016/0270673 A1 Sep. 22, 2016

(30) Foreign Application Priority Data  
Nov. 8, 2013 (EP) .................................... 13192108

(51) Int. Cl.  
*A61B 5/0225* (2006.01)  
*A61B 5/022* (2006.01)  
(Continued)

(52) U.S. Cl.  
CPC ........ *A61B 5/02255* (2013.01); *A61B 5/0225* (2013.01); *A61B 5/02208* (2013.01);  
(Continued)

(58) Field of Classification Search  
CPC ...... A61B 5/02208; A61B 5/022–0235; A61H 31/005  
See application file for complete search history.

(56) References Cited

U.S. PATENT DOCUMENTS 3,550,582 A * 12/1970 Wilhelmson ....... A61B 5/02208  
600/496  
3,552,383 A 1/1971 Krueger et al.  
(Continued)

FOREIGN PATENT DOCUMENTS

JP S49033874 9/1974  
JP S6179441 A1 4/1986  
(Continued)

OTHER PUBLICATIONS

Neumar et al. "Part 8: Adult Advanced Cardiovascular Life Support, 2010 American Heart Association Guidelines for Cardiopulmonary Resuscitation and Emergency Cardiovascular Care." Circulation. 2010;122:S729-S767. Originally published Oct. 17, 2010.*  
(Continued)

*Primary Examiner* — Meredith Weare (57) ABSTRACT

A device is configured for tracking e.g. the diastolic blood pressure in a patient. The device applies a pressure to a body part, e.g. by use of an inflatable cuff. By performing repeated and alternating pressure changes in the cuff, a specific feature of a signal that relates to the diastolic blood pressure can be tracked and possibly measured. The device may have particular use in conjunction with cardiopulmonary resuscitation devices.

16 Claims, 7 Drawing Sheets

(51) Int. Cl.
*A61B 7/04* (2006.01)
*A61B 7/00* (2006.01)
*A61B 5/0402* (2006.01)
*A61H 31/00* (2006.01)
*A61B 5/0456* (2006.01)
*A61B 90/00* (2016.01)

(52) U.S. Cl.
CPC ........ *A61B 5/02225* (2013.01); *A61B 5/0402* (2013.01); *A61B 7/00* (2013.01); *A61B 7/045* (2013.01); *A61H 31/005* (2013.01); *A61B 5/0456* (2013.01); *A61B 2090/378* (2016.02); *A61H 2230/305* (2013.01)

(56) References Cited

U.S. PATENT DOCUMENTS

| | | | |
|---|---|---|---|
| 4,252,127 A * | 2/1981 | Gemelke | A61B 5/02208 128/900 |
| 4,338,949 A * | 7/1982 | Croslin | A61B 5/02225 600/490 |
| 4,473,080 A * | 9/1984 | Paavola | A61B 7/045 600/491 |
| 4,549,549 A | 10/1985 | Furukawa | |
| 5,243,991 A * | 9/1993 | Marks | A61B 5/02233 128/DIG. 15 |
| 5,261,413 A | 11/1993 | Kawahara | |
| 5,873,836 A * | 2/1999 | Kahn | A61B 5/02141 600/490 |
| 5,876,348 A | 3/1999 | Sugo et al. | |
| 6,251,080 B1 * | 6/2001 | Henkin | A61B 5/02233 600/490 |
| 6,258,037 B1 * | 7/2001 | Dowling, Jr. | A61B 5/02208 600/490 |
| 7,569,018 B1 | 8/2009 | Geddes et al. | |
| 7,782,193 B2 | 8/2010 | Goh et al. | |
| 2006/0270952 A1 | 11/2006 | Freeman et al. | |
| 2007/0055163 A1 * | 3/2007 | Asada | A61B 5/02225 600/485 |
| 2007/0232939 A1 | 10/2007 | Forstner | |
| 2009/0076398 A1 | 3/2009 | Li et al. | |
| 2009/0318828 A1 * | 12/2009 | Hersh | A61B 5/022 600/561 |
| 2010/0094140 A1 | 4/2010 | Pranevicius et al. | |
| 2011/0224559 A1 | 9/2011 | Chen | |
| 2012/0010543 A1 * | 1/2012 | Johnson | A61N 1/3925 601/41 |
| 2012/0277597 A1 | 11/2012 | Eshvaugh et al. | |
| 2013/0303923 A1 * | 11/2013 | Lerner | A61B 5/02208 600/492 |
| 2015/0164417 A1 * | 6/2015 | Tupin, Jr. | A61B 5/0205 600/407 |

FOREIGN PATENT DOCUMENTS

| | | |
|---|---|---|
| JP | S61119240 A | 6/1986 |
| JP | 2009233284 A | 10/2009 |
| JP | 2011224080 A | 11/2011 |

OTHER PUBLICATIONS

Berg, R.A., et al., Adverse Hemodynamic Effects of Interrupting Chest Compressions for Rescue Breathing During Cardiopulmonary Resuscitation for Ventricular Fibrillation Cardiac Arrest. Circulation, 2001. 104: p. 2465-2470.

Eberle, B., et al., Checking the carotid pulse check: diagnostic accuracy of first responders in patients with and without a pulse. Resuscitation, 1996. 33(2): p. 107-16. Abstract.

Grmec, S., et al., Utstein style analysis of out-of-hospital cardiac arrest—bystander CPR and end expired carbon dioxide. Resuscitation, 2007. 72: p. 404-14. ABSTRACT.

Paradis, N.A., et al., Coronary perfusion pressure and the return of spontaneous circulation in human cardiopulmonary resuscitation. JAMA, 1990. 263(8): p. 1106-13. Abstract.

Rivers, E.P., et al., The clinical implications of continuous central venous oxygen saturation during human CPR. Ann Emerg Med, 1992. 21(9): p. 1094-101. Abstract.

Losert, H., et al., Thoracic-impedance changes measured via defibrillator pads can monitor signs of circulation. Resuscitation, 2007. 73: p. 221-228. Abstract.

Reynolds, J.C., et al., Tissue oximetry by near-infrared spectroscopy in a porcine model of out-of-hospital cardiac arrest and resuscitation. Resuscitation, 2012. Abstract.

Hodgkin, B.C., D.E. Burkett, and E.B. Smith, Noninvasive measurement of systolic and diastolic blood pressure in swine. Am J Physiol, 1982. 242(1): p. H127-30. Abstract.

Sutton, R.M., et al., Hemodynamic directed CPR improves short-term survival from asphyxia-associated cardiac arrest. Resuscitation, 2013. 84(5): p. 696-701. Abstract.

* cited by examiner

APPARATUS FOR TRACKING A SPECIFIC BLOOD PRESSURE

This application is a national stage application under 35 U.S.C. § 371 of International Application No. PCT/IB2014/059384 filed on Mar. 3, 2014 and published in the English language on May 14, 2015 as International Publication No. WO/2015/068053, which claims priority to EP Application No. 13192108.2 filed on Nov. 8, 2013, the entire disclosures of which are incorporated herein by reference.

FIELD OF THE INVENTION

The invention relates to measurement of blood pressures, particularly to non-invasive measurement and tracking of specific blood pressure features.

BACKGROUND OF THE INVENTION

There is a lack of non-invasive devices capable of performing fast, repeated measurements of blood pressures features such as the diastolic blood pressure, the mean blood pressure and the systolic blood pressure. Known devices may either be too complex, too expensive, too slow or inaccurate in order to be usable for certain purposes.

One purpose of such a blood pressure measurement device is for use with cardio pulmonary resuscitation (CPR) applied to a cardiac arrest victim where certain features of blood pressure measurements may be useful for assessing the quality of the CPR. Having repeated fast measurements allows for multiple assessments of CPR quality in a certain time frame.

Such blood pressure measurements might also be used to assess whether CPR was effective in restoring the subject's own heartbeat. Detection of the presence of a life sustaining pulse is a key action in determining if a subject's heart is beating spontaneously, and therefore if CPR has been successful. The point at which the heart starts to spontaneously generate life-sustaining blood flows again is known as the return of spontaneous circulation (ROSC). Determining ROSC is usually done by pausing CPR and performing manual palpation. However; this process is time-consuming and the resulting interruptions can negatively impact the outcome of the CPR. High-quality CPR requires minimizing interruptions to the chest compressions. Furthermore, manual palpation is known to be unreliable even if performed by expert clinicians, and even when a pulse is present it is often very difficult to determine if it is life sustaining. Monitoring of end-tidal $CO_2$, invasive blood pressure, or central venous oxygen saturation allows for a more objective assessment of ROSC, but are invasive as all require a secured airway or the placement of catheters. Trans-thoracic impedance (TTI) measurements and near-infrared spectroscopy (NIRS) are non-invasive, but TTI is strongly influenced by chest compressions and NIRS responds slowly upon ROSC. It would therefore be desirable to have a non-invasive, rapid and objective way of determining ROSC.

Further, trends of certain blood pressure features (e.g. diastolic, mean and systolic levels) can be used as an indicator of hemodynamic instability. Monitoring hemodynamic stability is especially important in critical and emergency care (e.g. for ICU patients and patients undergoing surgery or resuscitation). A (semi-)continous time series of at least one pulse pressure feature is necessary to ensure hemodynamic stability, or to detect deterioration. Currently hemodynamic stability has to be measured using invasive blood pressure catheters or using devices that cannot measure absolute pressures.

Accordingly there is a need for a non-invasive blood pressure measurement device capable of (semi-)continuously measuring blood pressure features such as the diastolic, mean and systolic blood pressures. Preferably, such a device would also be capable of performing fast and accurate tracking and measurements of blood pressure features.

US2010/0094140 discloses a method to measure intravascular or other compartment pressure by applying extrinsic pressure oscillations. Pressure-volume response of the compressed structure is obtained and compartment pressure is estimated as the extrinsic pressure at which compressed structure has the highest compliance. By delivering extrinsic oscillations at a higher frequency than the pulse rate, pressure reading can be obtained much faster. Because it is not dependant on intrinsic vascular oscillations, pressure can be measured during arrhythmias, during cardiac bypass, during resuscitation, in the venous compartment or in the other non-pulsatile compressible body compartments.

SUMMARY OF THE INVENTION

It would be advantageous to achieve improvements within devices for blood pressure measurements. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a blood pressure measurement device for performing repeated measurements and tracking of a distinctive blood pressure level in a blood vessel in a body part is presented that comprises, a pressure control unit for controlling a pressure providing device to apply an external pressure to the body part, a detector unit for detecting appearance of a physical characteristic indicative of the distinctive blood pressure level, wherein the device is configured to:

(i) control the pressure control unit to change the external pressure in a first direction until the physical characteristic has been detected;

(ii) in response to the detection of the physical characteristic, measure the external pressure between the body part and the pressure providing device by use of a pressure sensor connected to the pressure providing device so as to provide a measure of the distinctive blood pressure level;

(iii) in response to the detection of the physical characteristic, control the pressure control unit to change the external pressure in the direction opposite to the first direction until the physical characteristic is no longer detected; and (iv) cyclically repeat (i), (ii) and (iii) to produce a signal that tracks the distinctive blood pressure level over time.

The pressure sensor which may or may not be part of the blood pressure measurement device may for example be fluidly connected to the pressure providing device via a hose so that the pressure provided by the pressure providing device, e.g. an inflatable cuff, is also present in the hose. The pressure sensor may further be fluidly connected to the pressure control unit.

Advantageously, the cyclic change of the external pressures may enable fast and accurate tracking and measurement of blood pressure features.

In an embodiment the the distinctive blood pressure level is the diastolic blood pressure, and changing the external pressure in the first direction comprises applying the external pressure at a level which is at or near atmospheric pressure and then increasing the external pressure, and changing the external pressure in the direction opposite to the first direction comprises decreasing the external pressure.

In an embodiment the distinctive blood pressure level is the systolic blood pressure, and changing the external pressure in the first direction comprises applying the external pressure at a level above systole and then decreasing the external pressure, and changing the external pressure in the direction opposite to the first direction comprises increasing the external pressure.

In an embodiment the physical characteristic comprises one of: the appearance of a characteristic sound from the blood vessel or the disappearance of a characteristic sound from the blood vessel, and the detector unit is configured for detecting the characteristic sound.

In an embodiment, the distinctive blood pressure level is one of: diastolic blood pressure, systolic blood pressure and mean blood pressure level.

In an embodiment the physical characteristic is a particular oscillation amplitude in an oscillation in the external pressure measured by the pressure sensor, and the detector unit is configured to detect the particular oscillation amplitude.

In an embodiment the physical characteristic is a characteristic ultrasound reflection from the blood vessel, and the detector unit is configured to detect the characteristic ultrasound reflection.

In an embodiment the physical characteristic is a characteristic amplitude of a photoplethysmograph (PPG) waveform, and the detector unit is configured to detect the characteristic PPG waveform amplitude.

In an embodiment the physical characteristic is a characteristic morphology of a photoplethysmograph (PPG) waveform, and the detector unit is configured to detect the characteristic PPG waveform morphology.

In an embodiment the detector unit is configured to detect a validity of the physical characteristic as a function of an amplitude, a duration or a spectral content of a signal containing the physical characteristic. Advantageously, this detection of validity may be used to filter out artefacts in the physical characteristic, e.g. characteristic sounds.

In an embodiment the device is configured to control the pressure control unit to change the external pressure over a pressure range, wherein the device is configured to determine a maximum oscillation amplitude present within the pressure range, and wherein the device is configured to set the particular oscillation amplitude as the maximum oscillation amplitude or to set the particular oscillation amplitude as a fraction of the maximum oscillation amplitude 401.

In an embodiment the device is configured to change the rate of change of the external pressure in the first and/or second pressure changes in response to a request.

In an embodiment the detector unit is configured to detect the physical characteristic as a function of an input signal containing information about timing of chest compressions applied to a cardiac arrest victim.

In an embodiment the detector unit is configured to detect the physical characteristic as a function of an input signal containing information about timing of an electrocardiogram (ECG).

In an embodiment the device is adapted to determine return of spontaneous circulation, ROSC, and further comprises a processing unit configured to:

receive data from the detector unit;

generate an at least semi-continuous time series of values for the distinctive blood pressure level using the received data; and determine ROSC by comparing the generated time series with at least one predefined criterion.

In an embodiment the at least one predefined criterion comprises a predefined threshold for the distinctive blood pressure level.

In an embodiment the at least one predefined criterion additionally comprises a predefined minimum time for which this threshold must be exceed by contiguous values in the time series.

In an embodiment the device is configured to generate an alarm in response to a positive determination of ROSC.

A second aspect of the invention relates to a CPR device configured for applying chest compressions to a cardiac arrest victim, wherein the CPR device comprises the device according to the first aspect.

In an embodiment the CPR device comprises a compression depth monitor configured to determine chest compression depth waveform or timing of chest compressions.

In an embodiment the CPR device is configured to determine a quality parameter of the performed chest compressions by use of the distinctive measured blood pressure level.

In an embodiment the CPR device is configured to adapt chest compression as a function of the quality parameter.

In an embodiment the CPR device is configured to detect return of spontaneous circulation, ROSC, based on the distinctive measured blood pressure level.

In an embodiment the CPR device is configured to adapt chest compression in response to detecting ROSC.

In an embodiment the CPR device is configured to generate an alarm in response to detecting ROSC.

A third aspect of the invention relates to a method for tracking a distinctive blood pressure level in a blood vessel in a body part, wherein the method comprises, (a) applying an external pressure to the body part, (b) changing the external pressure applied to the body part in a first direction until a physical characteristic indicative of the distinctive blood pressure level has been detected, (c) in response to the detection of the physical characteristic, measuring the external pressure between the body part and the pressure providing device so as to provide a measure of the distinctive blood pressure level, (d) in response to the detection of the physical characteristic, changing the external pressure applied to the body part in the direction opposite to the first direction until the physical characteristic is no longer detected; and (e) cyclically repeating steps (b), (c) and (d) to produce a signal that tracks the distinctive blood pressure level over time.

The method of the third aspect may be supplemented by the step of measuring the external pressure between the body part and the pressure providing device by use of a pressure sensor connected to the pressure providing device so as to provide a measure of the distinctive blood pressure.

A fourth aspect of the invention relates to computer program product comprising program code instructions which when executed by a processor enables the processor to carry out the method of the third aspect.

Another aspect of the invention relates to a computer-readable medium comprising a computer program product according to the fourth aspect. The computer-readable medium may be a CD, a memory, an electronic circuit or other physical medium capable of storing data. Thus, in general the computer-readable medium may be a non-transitory medium.

In general the various aspects of the invention may be combined and coupled in any way possible within the scope of the invention. These and other aspects, features and/or advantages of the invention will be apparent from and elucidated with reference to the embodiments described hereinafter.

In summary the invention relates to a device configured for tracking certain blood pressure features, e.g. the diastolic blood pressure in a patient. The device applies a pressure to a body part, e.g. by use of an inflatable cuff. By performing repeated and alternating pressure changes in the cuff a specific feature of a signal that relates to the blood pressure feature can be tracked and possibly measured.

BRIEF DESCRIPTION OF THE DRAWINGS

Embodiments of the invention will be described, by way of example only, with reference to the drawings, in which.

DESCRIPTION OF EMBODIMENTS

Figure 1:
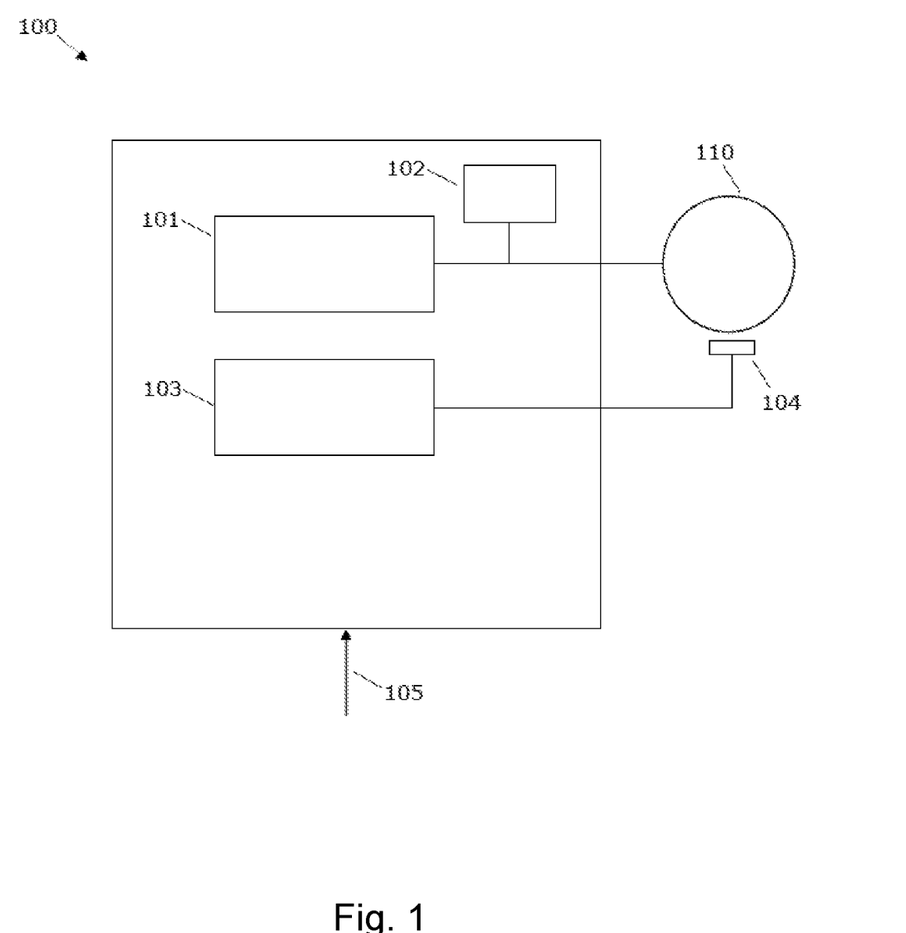
FIG. 1 illustrates a blood pressure measurement device 100.

FIG. 1 illustrates a blood pressure measurement device 100 configured to perform repeated measurements and tracking of blood pressure features in a blood vessel in a body part of a human, or for that matter, a mammal. Blood pressure features comprise diastolic blood pressure, mean blood pressure, systolic blood pressure and other blood pressure features. The body part is typically the upper arm at the level of the heart when a person is in a standing position, but may also be the ankle or other suitable body part. The distinctive blood pressure levels are typically the diastolic blood pressure level, the mean blood pressure level and optionally also the systolic blood pressure level.

The device 100 comprises a pressure control unit 101 for controlling a pressure providing device 110 to apply an external pressure to the body part. The pressure providing device 110 is typically an inflatable cuff and the pressure control unit 101 may be a controllable air-pump which can inflate or deflate the cuff via a hose connection. However, the pressure control unit 101 could also be configured to supply a control signal (e.g. an electrical control signal) to an air-pump connected to a cuff 110.

The device 100 may further comprise a pressure sensor 102 configured for measuring the pressure between the body part and the pressure providing device 110, e.g. the pressure present in a hose connection used for inflating the cuff. The measured pressure consists of a combination of the externally applied pressure and the pressure exerted by the body part on the pressure providing device. The pressure sensor may be an air pressure sensor configured to measure the pressure in the cuff so as to obtain a measure of the externally applied pressure and the pressure exerted by the body part. For example, the air pressure sensor may be connected with a hose connection provided between the pressure control unit 101 and the pressure providing device 110. The pressure sensor 102 may be part of the device 100 or the device 100 may be connectable with the pressure sensor 102. For example, the pressure sensor 102 may be part of an air pump which is not part of the device 100, but which is controllable by the pressure control unit 101.

Accordingly, an applied external pressure is applied to the body part via the pressure providing device 110, and the external pressure present between the body part and the pressure providing device 110 is measured by a pressure sensor 102. The measured external pressure is used for determining a blood pressure.

The device 100 comprises a detector unit 103 for detecting appearance of a physical characteristic indicative of the distinctive blood pressure level, e.g. the diastolic, mean or systolic blood pressure. For example, the physical characteristic may be the (dis-) appearance of a characteristic sound, e.g. Korotkoff sounds, occurring from a blood vessel in the body part. As these sounds occur between systole and diastole, the (dis-)appearance of sounds occurs when the applied external pressure equals the systolic (level 1 Korotkoff) or the diastolic blood pressure (level 4 or 5 Korotkoff). Details of this example are described in below. According to this example, the detector unit 103 is configured for detecting such characteristic sounds. For example, the detector unit 103 may comprise an audio processing function capable of detecting presence of particular sounds in a signal from a microphone 104. Accordingly, the detector unit 103 may be connectable with a microphone 104 or may comprise a microphone 104. The microphone is designed to be placed on the body part over an artery. For example, the microphone may be integrated with the cuff 110 or designed to be used with the cuff 110.

In another example, the physical characteristic is a particular oscillation amplitude in an oscillation in the pressure measured by the pressure sensor 102. Details of this example are described below. According to this example, the detector unit 103 is configured for detecting such oscillation amplitudes via a pressure measurement signal provided by the pressure sensor 102. For example, the detector unit 103 may comprise a signal processing function configured to detect amplitudes in an oscillation signal. In this case the detector 104 may not be used.

In another example, the physical characteristic is a characteristic ultrasound reflection from the blood vessel. According to this example, the detector unit 103 is configured to detect such characteristic ultrasound reflections, e.g. by means of a signal processing function configured to detect signals from an ultrasound probe, i.e. a device which transmits ultrasounds and receives reflections or echoes of the transmitted ultrasound. Accordingly, the detector unit 103 may be connectable with an ultrasound probe or may comprise an ultrasound probe 104. The ultrasound probe is designed to be placed on the body part over an artery. For example, the ultrasound probe may be integrated with the cuff 110 or designed to be used with the cuff 110.

In another example, the physical characteristic is a characteristic amplitude of a photoplethysmograph (PPG) waveform. Alternatively the physical characteristic can be a characteristic morphology of a PPG waveform. According to this example, the detector unit 103 is configured to detect such characteristic PPG amplitudes and/or morphologies, e.g. by means of a signal processing function configured to detect signals from a PPG sensor (i.e. a device which illuminates the skin and measures changes in light absorption due to blood volume changes in the illuminated region). Accordingly the detector unit 103 may be connectable with a PPG sensor. The PPG sensor is designed to be placed distal of the cuff 110 (e.g. at a finger).

The device 100 may further be configured to receive an external input signal 105 containing information about expected timing of a physical characteristic of the distinctive blood pressure level. The input signal 105 may be used by the device 100, e.g. by the detector unit 103, for detecting the appearance of the physical characteristic at a certain time delay relative to signal features in the input signal 105. Using this input signal 105 may enhance the robustness of detection of a physical characteristic. Especially when the physical characteristic is not present, the input signal 105 and time delay may give conclusive information about this characteristic not being present. Without this input signal 105, the detection of a characteristic not present is not straight forward, as it is not known when a physical characteristic should not occur.

For example, the external input signal 105 can contain R-peaks from the electrocardiogram (ECG) of a patient. The occurrence of a sound at the microphone 104 is expected at a certain time delay from each R-peak. When a R-peak is not followed by a physical characteristic within a certain time frame around the expected time delay, or when a R-peak is followed by another R-peak, the absence of the physical characteristic is clear.

In another example for use during CPR, the external input signal 105 can contain timing information of chest compression depths (e.g. the start of compressions), as R-peaks are absent in cardiac arrest patients.

For the purpose of being able to track a distinctive blood pressure level, the device 100 is configured for controlling the pressure control unit 101 to increase the applied external pressure in a first pressure change at least until the appearance of the physical characteristic has been detected, and configured to decrease the external pressure in a second pressure change at least until the physical characteristic is not present anymore. After a certain point in time when the physical characteristic is not detected anymore, the applied external pressure is increased again, in the first pressure change, at least until the physical characteristic is detected again.

Due to this repetitive change of the external pressure through alternating first and second pressure changes the distinctive blood pressure level is tracked in an at least semi-continuous way.

Since the change in the applied external pressure is invoked at the point in time when the physical characteristic appears or disappears or at a short delay thereafter, only small changes in the applied external pressure are required for tracking purposes so that only little time is present between successive detections of the distinctive blood pressure level. Thus, the applied external pressure need not cycle between extreme distinctive blood pressure values such as between the diastolic and systolic pressures.

In a repetitive change of the applied external pressure, wherein the applied external pressure is increased in a first pressure change at least until the appearance of the physical characteristic has been detected, the distinctive blood pressure may be a low blood pressure level such as the diastolic pressure level.

Alternatively or additionally, the device 100 may similarly be configured for controlling the pressure control unit 101 to decrease the external pressure in a first pressure change at least until the appearance of the physical characteristic has been detected, and configured to increase the external pressure in a second pressure change at least until the physical characteristic is not present anymore. This repetitive change of the external pressure may be suited for detecting high pressure levels such as the systolic pressure level.

In general the first pressure change may be seen as a change for detecting start of a physical characteristic and the second pressure change may be seen as a change for removing the physical characteristic from the signal monitored by the detector unit 103.

In order to determine the blood pressure, the device is configured to measure the external pressure between the body part and the pressure providing device 110 by use of a pressure sensor 102 connected to the pressure providing device 110. The measurement is in response to the detection of the appearance of the physical characteristic so as to determine the distinctive blood pressure.

For example, the device may be configured to read the pressure from the pressure sensor at the point in time when the appearance of the physical characteristic is detected so as to provide a measure of the distinctive blood pressure.

That is, when the physical characteristic is present, e.g. appearance of the Korotkoff sound, the distinctive blood pressure level, e.g. the diastolic blood pressure, can be assumed to be equal or approximately equal to the external pressure measured by the pressure sensor 102. Thus, in response to the detection of the appearance of the physical characteristic the distinctive blood pressure level can be set to the measured external pressure. In this way, the physical characteristic is indicative of the distinctive blood pressure level.

Figure 2:
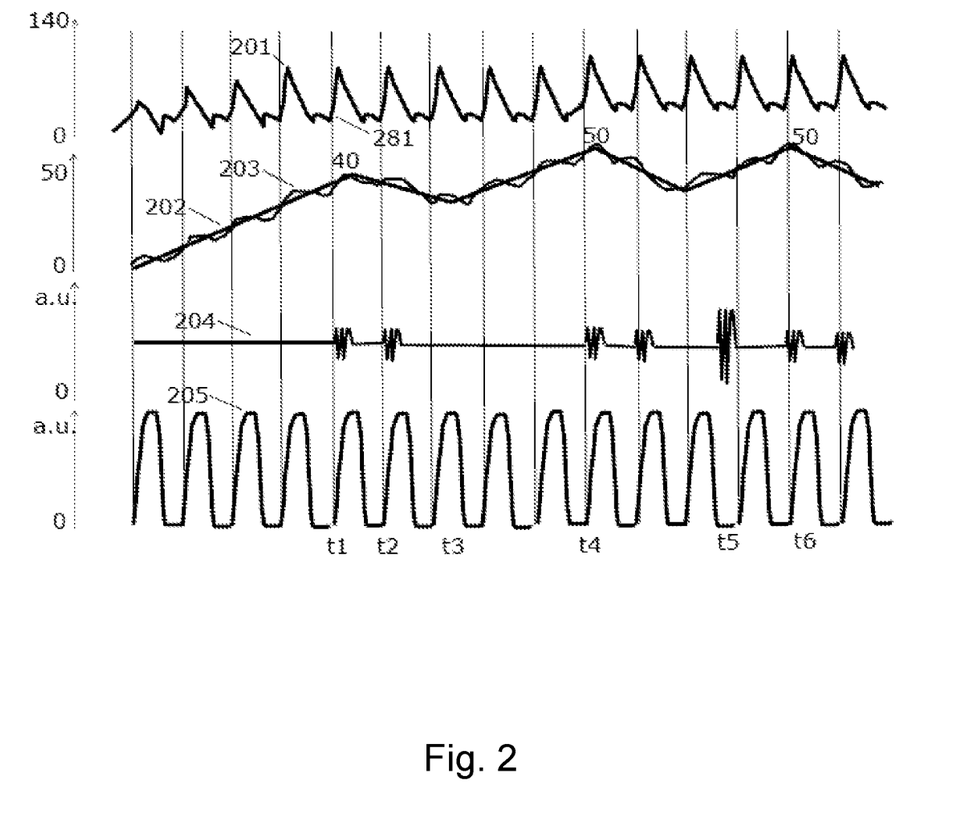
FIG. 2 illustrates tracking of a diastolic blood pressure by use of characteristic sounds 204.

In order to illustrate tracking of a particular blood pressure level an example is illustrated in FIG. 2 wherein sound measured from an artery is used as a physical characteristic for indicating when the measured pressure is equal to diastolic blood pressure.

FIG. 2 shows the invasive blood pressure 201 (shown as a reference pressure) on a 0-140 mmHg pressure scale, the applied external pressure 202 (e.g. cuff pressure) together with blood pressure oscillations 203 measured by the pressure sensor 102 on a 0-50 mmHg pressure scale, sound level 204 measured from an artery using a microphone 104 and chest compression depth measurements 205 from chest compressions given to a cardiac arrest victim (the measurements 205 may be provided to the device 100 via the input 105).

In FIG. 2 the oscillations 203 are present because of the chest compressions 205.

The cuff pressure (in this example a traditional inflatable cuff is used to provide an applied external pressure) is initially increased from 0 mmHg. At time t1 a characteristic sound (the Korotkoff level 4 sound) is detected by the detector unit 103 and microphone 104. At time t1 the cuff pressure 202 is 40 mmHg and, therefore, the diastolic blood pressure (the distinctive blood pressure) is 40 mmHg. After time t1 the cuff pressure is decreased. Here an optional delay is shown after time t1 before the cuff pressure is decreased. In general the delay may be substantially zero or a large delay may be used. At time t2 during the pressure decrease another Korotkoff sound is detected since the cuff pressure 202 is still higher than the diastolic pressure (indicated by reference 281). The cuff pressure is decreased further until time t3 where the characteristic sound is no longer present, which may be detected because at a certain time delay from the start of compressions at input 105, no characteristic sound has occurred. After time t3 the cuff pressure is increased again until time t4 where the characteristic sound is detected again, now at an increased cuff pressure at 50 mmHg. The alternating pressure changes are repeated so that the diastolic blood pressure is tracked (at time t6 a new diastolic blood pressure at 50 mmHg is detected).

Predetermined time periods may be associated with the first and second pressure changes. For example, a minimum duration may be set from detection of the appearance of the physical characteristic (e.g. at time t1) until the applied external pressure is changed again from increasing/decreasing to decreasing/increasing, e.g. in order to verify the presence of the physical characteristic in a next heartbeat or compression. Further, a minimum duration may be set from start of the second pressure change until start of the subsequent first pressure change, or from the point when no physical characteristic is present anymore in the second pressure change until start of the subsequent first pressure change.

The blood pressure tracking device 100 may be configured to change the rate-of-change of the applied external pressure in the first and/or second pressure changes in response to a request. The request may be in the form of an input signal to the device 100 generated in response to a user interface input from a user of the device, or the request may be in the form an input signal generated by an adaptive function of the device 100. For example, the user interface may be configured to enable the user to change the inflation and/or deflation rate of the pressure providing device 110, in order to have faster tracking (at the cost of decreased precision). The adaptive function may be a function which controls rate-of-change of the applied external pressure in response to e.g. the input signal 105 containing information about timing of chest compressions, in response to variations in measured blood pressures, or other information, e.g. information relating to the tracking performance of the device 100.

FIG. 2 shows that at time t5 a faulty sound is detected which should not be classified as a characteristic sound. In order to avoid such false positive errors the detector unit 103 may be configured for detecting validity of a characteristic sound as a function of one or more of the following characteristics: Sound amplitude (zero level or other particular amplitude), sound duration and spectral content of the sound (detector unit or device is configured for determining sound amplitude, sound duration or spectral content of the sound). For example, a filter of the detector unit 103 may be configured to only make a positive detection of sound amplitudes above a certain amplitude threshold, or sound amplitudes which are above and below certain thresholds. Similarly, the detector unit 103 may be configured to only categorise a sound measurement as a characteristic sound, if the duration of a characteristic sound continues for a certain minimum time or if spectral content of the sound is within certain spectral ranges. Any of these filtering methods may be combined.

FIG. 2 illustrates that the chest compression depth timing 205 may be used for classifying valid sound characteristics depending on the synchronisation between a sound sequence and the chest compression signal 205, e.g. by categorising a sound measurement as a valid characteristic sound if the sound starts (amplitude becomes greater than a given threshold) within a certain time frame wherein the compression signal 205 increases beyond zero. For that purpose the detector unit 103 or other unit of the device 100 may be configured for determining sound amplitude, sound duration or spectral content of the sound.

Thus, the detector unit 103 may be configured for detecting the appearance of the characteristic sound as a function of the input signal 105, 205 containing information about chest compression depth timing from chest compressions applied to a cardiac arrest victim. When a patient has a spontaneous heart beat and CPR doesn't need to be performed, R-peaks in an ECG signal might be used as input signal 105 instead of using the compression depth timing information.

Figure 3:
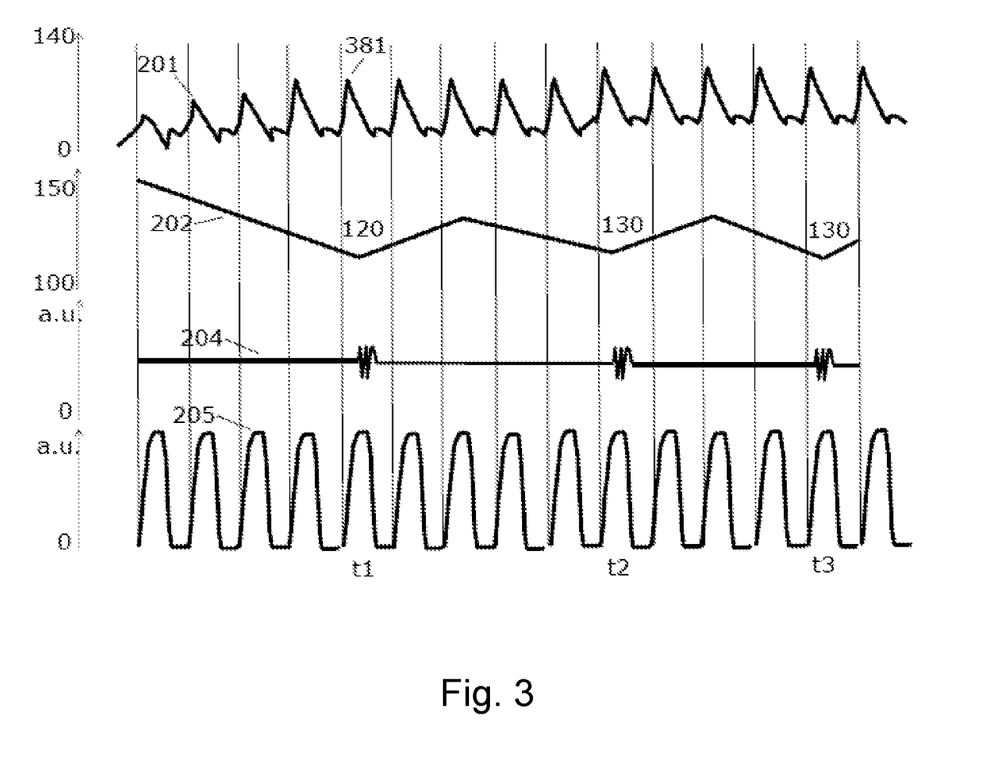
FIG. 3 illustrates tracking of a systolic blood pressure by use of characteristic sounds 204.

FIG. 3 shows the invasive blood pressure 201 (shown as a reference pressure) on a 0-140 mmHg pressure scale, the applied external pressure 202 (e.g. cuff pressure) on a 100-150 mmHg pressure scale, sound level 204 measured from an artery using a microphone 104 and chest compression depth measurements 205 from chest compressions given to a cardiac arrest victim (the measurements 205 may be provided to the device 100 via the input 105).

FIG. 3 illustrates an example for tracking of high blood pressures such as the systolic blood pressure.

The external pressure is initially decreased from a level above the systolic pressure. At time t1 a characteristic sound (the Korotkoff level 1 sound) is detected by the detector unit 103. At time t1 the measured cuff pressure 202 is 120 mmHg and, therefore, the systolic blood pressure 381 is 120 mmHg. After time t1 the external pressure is increased again, possibly after a delay, until the characteristic sound is no longer present, possibly with addition of a further delay as illustrated. Then the external pressure is decreased again until time t2 where the characteristic sound is detected again, now at an increased pressure of 130 mmHg. In this way the alternating pressure changes are repeated so that the systole blood pressure is tracked (at time t3 a new systolic blood pressure at 130 mmHg is detected). It is noted that low blood pressures such as the diastolic pressure, may also be tracked with alternating first and second pressure changes wherein the applied external pressure is decreased during the first pressure change. Similarly high blood pressures such as the systolic pressure may also be tracked with alternating first and second pressure changes wherein the external pressure is increased during the first pressure change. In both cases, the physical characteristic is the disappearance of Korotkoff sounds instead of the appearance of Korotkoff sounds.

Figure 4:
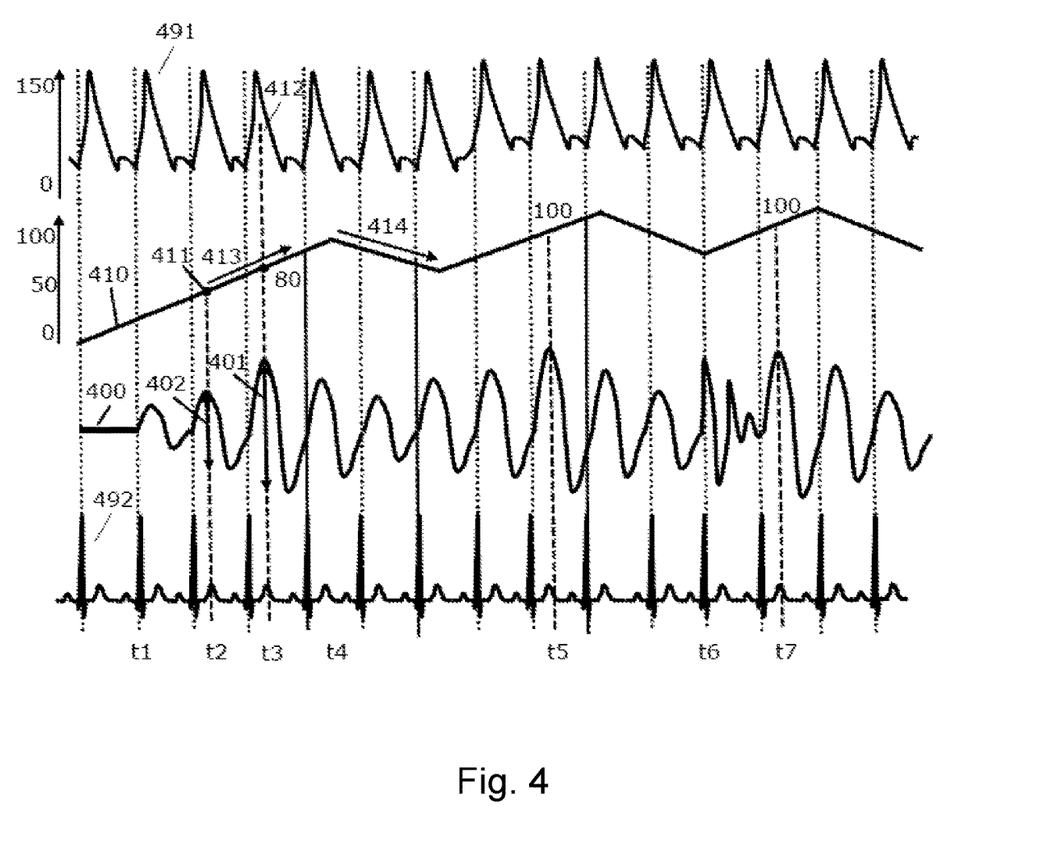
FIG. 4 illustrates tracking of a mean blood pressure level by use of maximum oscillation amplitude 401 in an oscillation measured by a pressure sensor.

FIG. 4 shows the invasive blood pressure 491 (shown as a reference pressure) on a 0-150 mmHg pressure scale, the applied external pressure 410 (e.g. cuff pressure) on a 0-100 mmHg pressure scale, pressure oscillations in the measured external pressure 400 measured by the pressure sensor 102 and ECG 492 from a patient (the measurements 492 may be provided to the device 100 via the input 105).

FIG. 4 illustrates an example for tracking of a distinctive blood pressure level (e.g. the mean blood pressure) by use of maximum oscillation amplitude 401 in an oscillation in the applied external pressure measured by the pressure sensor.

In order to determine the maximum oscillation amplitude, the applied external pressure 410 is initially increased from a low level (e.g. 0 mmHg). During the increase in applied external pressure, oscillations start at t1 and increase in amplitude up to the maximum amplitude 401 at the mean arterial pressure 412 (of 80 mmHg in this example) at t3. Further increasing the external applied pressure results in a decrease of the oscillation amplitude. When the maximum is detected by the next smaller oscillation at t4, the applied pressure is decreased and a further decrease in oscillation amplitude can be detected. After this decrease this inflation/deflation sequence is repeated and can be used to track the mean arterial pressure (at time t5 and t7 new, increased mean blood pressures of 100 mmHg are detected).

Instead of tracking the maximum oscillation amplitude, an absolute amplitude or a fraction of the maximum amplitude can be tracked. For example, after detection of the maximum amplitude 401, a specific amplitude fraction on either pressure levels above or below the pressure belonging to the maximum oscillation amplitude can be tracked. These specific fractions can be belong to certain blood pressure features (e.g. a fraction of 0.8 of the maximum amplitude could resemble the diastolic level 411 at pressures below the mean arterial pressure shown at t2 in FIG. 4, a fraction of 0.6 could resemble to systolic level at pressure levels above the mean arterial pressure). Before being able to detect the fraction of the maximum oscillation amplitude the maximum oscillation amplitude should be determined first.

Accordingly, in order to determine one or more particular oscillation amplitude fractions the device 100 or other unit of the device 100 is configured to set the maximum oscillation amplitude 401, where after the amplitude fraction of measured oscillations (e.g. amplitude fraction 402) can be determined in order to control the pressure providing device 110 to provide alternating increases and decreases in the applied external pressure.

Further, in order to determine the maximum oscillation amplitude 401, the device 100 may be configured for controlling the pressure control unit 101 to change the applied external pressure over a pressure range. Further, the device may be configured to determine the maximum oscillation amplitude 401 present within the pressure range, e.g. by use of a peak detection method.

For the purpose of being able to track a distinctive blood pressure level 411, by use of a particular oscillation amplitude 402 the device 100 is configured for controlling the pressure control unit 101 to apply first and second pressure changes 413, 414 around one or more of the particular oscillation amplitudes 401, 402 similarly to the procedures described in connection with FIG. 2 and FIG. 3.

For example, the applied external pressure may be increased (alternatively decreased) in a first pressure change 413 at least until the appearance of the particular oscillation amplitude 401, 402 has been detected, and subsequently the applied external pressure is decreased (alternatively increased) in a second pressure change 414 at least until the particular oscillation amplitude 402 is not present anymore.

FIG. 4 shows that at time t6 a faulty pressure oscillation is detected. In order to avoid such false positive errors the detector unit 103 may be configured for detecting validity of a characteristic pressure oscillation as a function of one or more of the following characteristics: Oscillation amplitude, oscillation duration and spectral content of the oscillation (detector unit or device is configured for determining oscillation amplitude, oscillation duration or spectral content of the oscillation). For example, a filter of the detector unit 103 may be configured to only make a positive detection of oscillation amplitudes below a certain amplitude threshold. Similarly, the detector unit 103 may be configured to only categorise an oscillation as a valid oscillation if the spectral content of the oscillation is within certain spectral ranges. Any of these filtering methods may be combined.

FIG. 4 illustrates that the ECG 492 may be used for classifying valid oscillation characteristics depending on the synchronisation between a pressure oscillation and the ECG, e.g. by categorising an oscillation measurement as a valid characteristic oscillation if the oscillation starts (amplitude becomes greater than a given threshold) within a certain time frame where a peak in the ECG 492 is detected. For that purpose the detector unit 103 or other unit of the device 100 may be configured for determining oscillation amplitude, oscillation duration or spectral content of the oscillation.

When applying cardio pulmonary resuscitation (CPR) to a cardiac arrest victim the quality of the CPR is important to optimally resuscitate a patient. The CPR quality may be determined based on measured blood pressure values, e.g. measured diastolic pressure values.

It is also necessary to determine when the return of spontaneous circulation (ROSC) occurs, when applying CPR. The present inventors have found that certain levels of diastolic or mean blood pressure can be used to detect ROSC in a fast and reliable way. The existence of a strong relationship between measurements of the diastolic blood pressure and the carotid blood flow, and between measurements of the mean blood pressure and the carotid blood flow, has been demonstrated in a pig model, as will now be explained with reference to FIGS. 5 and 6.

Figure 5:
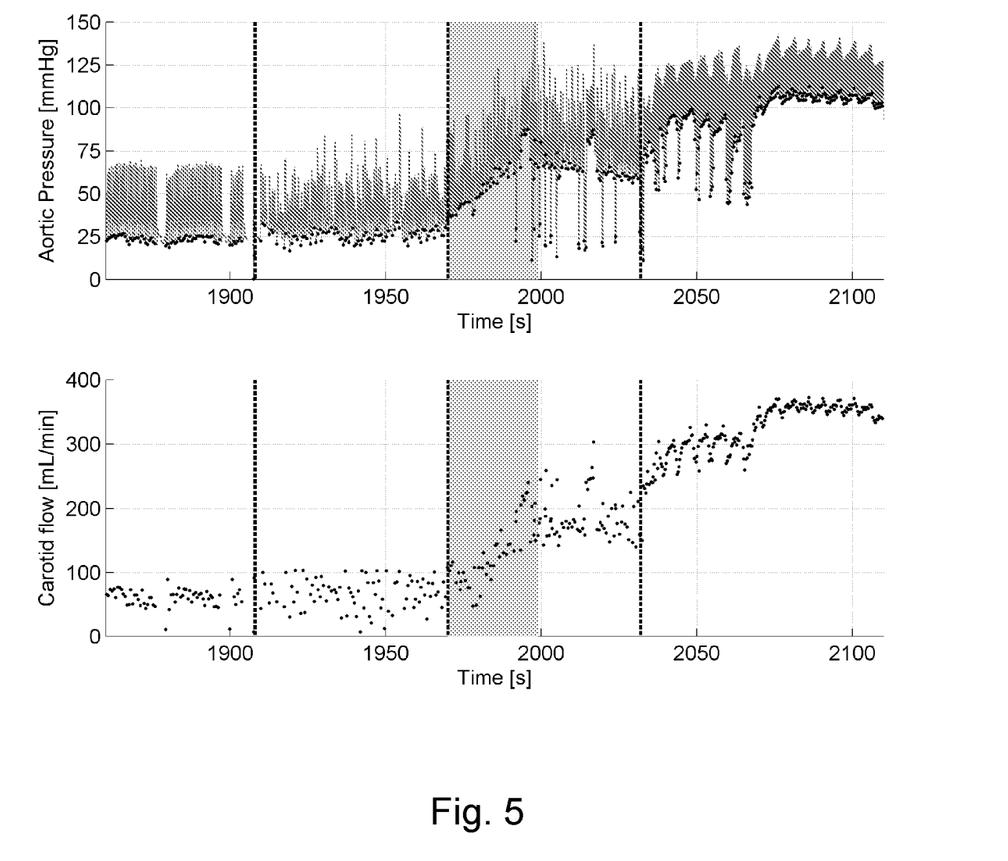
FIG. 5 shows a first example of an arterial blood pressure trace and a carotid flow trace for a pig model.

FIG. 5 shows an example of an arterial blood pressure trace during which ROSC appears after some time of CPR, for a pig model. The top trace shows aortic blood pressure over time, with dots indicating the diastolic value. The lower trace shows the carotid blood flow for the same time period, averaged over a compression/heartbeat. At the start of the trace the animal is in cardiac arrest and CPR is performed, which results in arterial pressures of 65/25 (65 systolic level, 25 diastolic level). At t=1907, compressions are paused and a defibrillation shock is given. Compressions are immediately restarted after the shock. The defibrillation shock does not result in spontaneous heart mechanical activity directly after the shock, as can be seen by the diastolic pressure level being similar to before the shock. However, the shock had some effect, causing the pattern of the blood pressure signal to become more irregular. At t=1970, the arterial blood pressure (both systolic and diastolic) starts to rise as a result of the defibrillation shock. The rise in diastole in this period is about a factor 3 (from 25 mmHg to 75 mmHg), which indicates a life sustaining own heartbeat. The rise in diastole takes place in about 30 seconds.

Depending on the threshold for ROSC/life sustaining pressures (which is an arbitrary value, however 60 mmHg is often used), the diastolic value is indicative for ROSC in this period. While ROSC was already achieved, compressions were still performed up to 2032 seconds (in real clinical resuscitations, compressions might go on for much longer without the recognition of ROSC). It can clearly be seen that the measured diastolic pressure closely resembles the carotid flow, which justifies the use of the diastolic blood pressure as a measure of blood flow, and thus in a method for determining ROSC.

Figure 6:
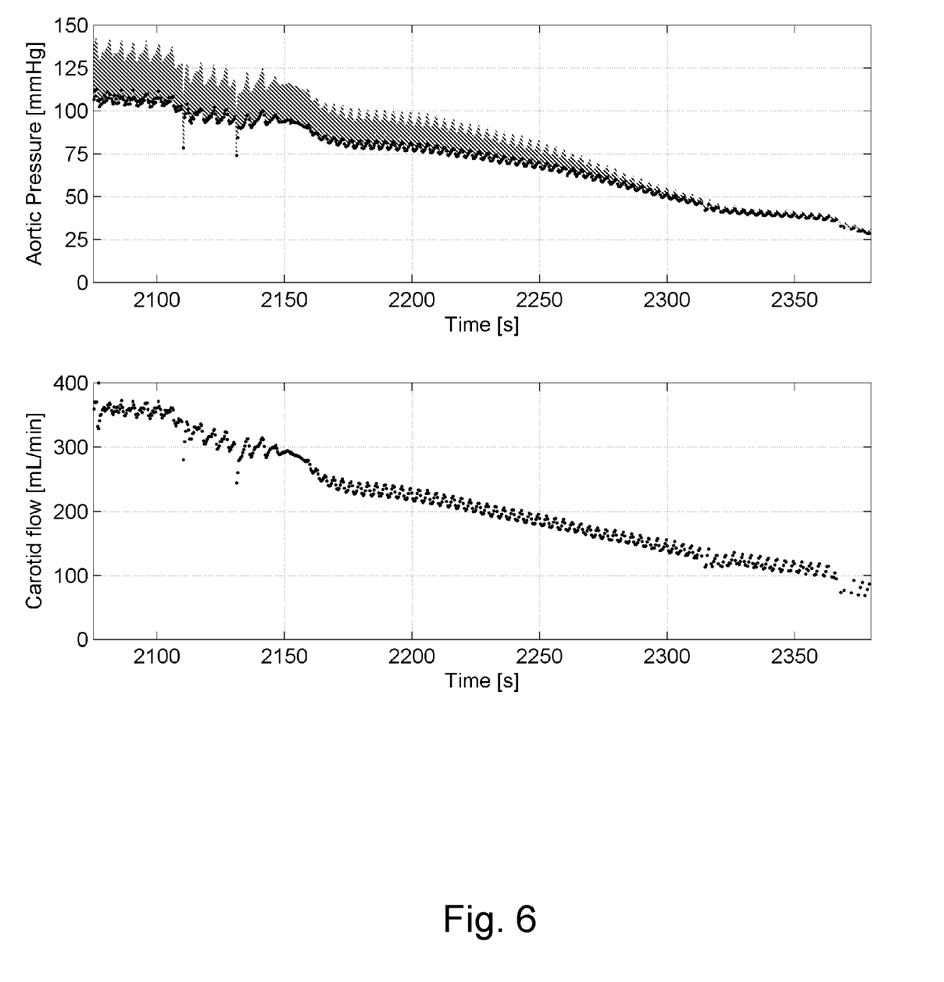
FIG. 6 shows a second example of an arterial blood pressure trace and a carotid flow trace for a pig model.

FIG. 6 shows an example of an arterial blood pressure trace in a deteriorating animal. As with FIG. 5, the top trace shows blood pressure over time, with dots indicating the diastolic value, and the lower trace shows the carotid blood flow for the same time period, averaged over a heartbeat. At start of the trace, the blood pressure is normal (125/100). Over time, both the systolic and diastolic values decrease and become life threatening. Again, it can clearly be seen that the measured diastolic blood pressure closely resembles the carotid flow, justifying the use of the diastolic blood pressure as a measure of hemodynamic (in-)stability.

The device 100 may therefore be used assess the hemodynamic stability of a subject, e.g. during surgery or in an intensive care unit. It may also be used during CPR, to determine whether the subject has obtained ROSC. Measurements of either the diastolic pressure (measured by detecting the appearance/disappearance of Korotkoff sounds with a microphone, by detecting specific fractions of pressure oscillations in the cuff, by detecting changes in ultrasound characteristics measured by an ultrasound probe, or by detecting the amplitude and/or morphology of a PPG waveform) or the mean blood pressure (measured by detecting pressure oscillations in the cuff) can be used for these purposes.

In an embodiment (not illustrated) adapted to determine ROSC during CPR, the device 100 further comprises a processing unit. The processing unit is configured to receive data from the detector unit 103 and to generate an at least semi-continuous time series of values for a blood pressure feature, based on the received data. The processing unit is further configured to determine whether predefined criteria for ROSC are met by the time series. For example, the predefined criteria may comprise a predefined threshold in a blood pressure feature (e.g. 60 mmHg), and a predefined minimum time (e.g. 15 seconds) for which this threshold must be exceeded. In some such embodiments the device 100 is configured to emit an alarm when ROSC has been determined.

CPR may be applied manually to a patient by a rescuer or automatically by a CPR device configured to apply chest compressions to a cardiac arrest victim by use of e.g. an electrically driven compression pad.

Figure 7:
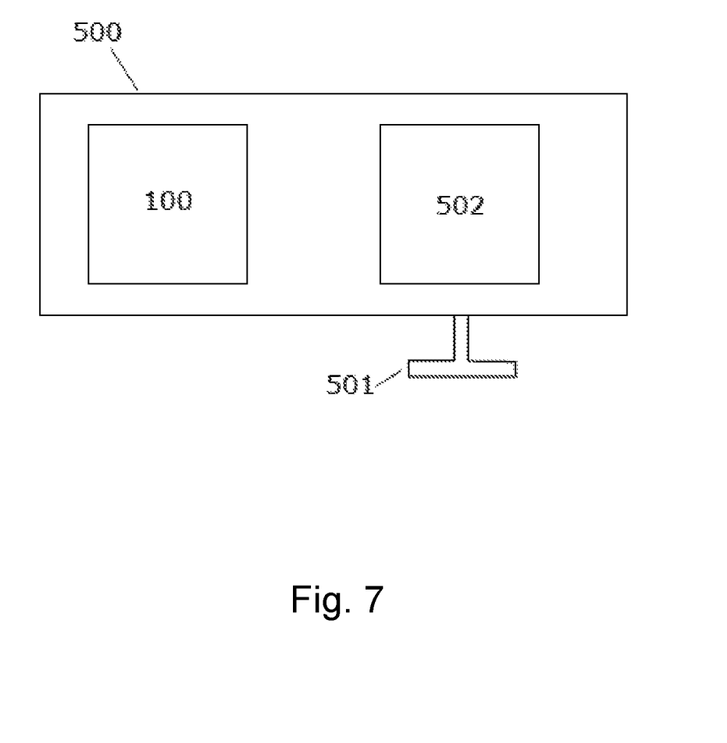
FIG. 7 shows a CPR device 500 configured to apply chest compressions to a cardiac arrest victim by use of a compression pad 501.

FIG. 7 shows a CPR device 500 configured to apply chest compressions to a cardiac arrest victim by use of a compression pad 501. The CPR device 500 comprises the blood pressure tracking and measurement device 100. This combination of a CPR device 500 and a blood pressure measurement device 100 may be advantageous since the quality of the applied chest compressions may be determined from repeated measurements of blood pressure.

The CPR device 500 may comprise a compression depth monitor 502 configured to determine the chest compression depth waveform or timing of chest compressions. The monitor 502 may be configured to measure the displacements of the compression pad 501. The determined chest compression depth waveform or timing of the compressions may be supplied to the device 100, e.g. via an input 105.

The CPR device 500 may be configured to determine a quality parameter of the performed chest compressions by use of the measured blood pressure levels. Furthermore, the CPR device may be configured to adapt chest compression as a function of the quality parameter. Alternatively or additionally, the CPR device 500 may be configured to determine ROSC by use of the measured blood pressure levels. Furthermore, the CPR device may be configured to adapt chest compression, or to cease chest compression, in response to a determination of ROSC. The CPR device may be configured to emit an alarm in response to a determination of ROSC.

Devices and methods according to embodiments of the invention can also be advantageously used for ambulatory blood pressure monitoring, in which blood pressure is measured at regular intervals over a given time period (e.g. 24 hours), as the subject goes about their normal daily life. In an embodiment (not illustrated) adapted to perform ambulatory blood pressure monitoring, the pressure control unit 101 of the device 100 is provided as a small portable unit attached to a belt arranged to be worn by the subject. The device 100 is arranged to continuously or semi-continuously measure a blood pressure feature (e.g. the diastolic blood pressure level) in the manner described above for the whole time period of the ambulatory blood pressure monitoring. By contrast, conventional ambulatory blood pressure monitoring systems are arranged to take measurements of diastolic and systolic blood pressure levels at periodic intervals (e.g. every 30 minutes). The device 100 therefore allows for the acquisition of a much more fine-grained picture of how the subject's blood pressure varies over the monitoring period.

A method according to an embodiment of the invention for tracking a distinctive blood pressure level in a blood vessel in a body part comprises the steps:

Step 1: Controlling a pressure providing device 110 for applying an external pressure to the body part.

Step 2: Measuring the applied external pressure between the body part and the pressure providing device, e.g. by use of the pressure sensor 102.

Step 3: Detecting appearance of a physical characteristic indicative of the distinctive blood pressure level.

Step 4: Controlling the pressure control unit to increase, alternatively decrease, the applied external pressure in a first pressure change at least until the appearance of the physical characteristic has been detected.

Step 5: Controlling the pressure control unit to decrease, alternatively, increase the applied external pressure in a second pressure change at least until the physical characteristic is not present anymore.

An optional step 6 includes determining a distinctive blood pressure when the appearance of the physical characteristic has been detected. This step is not required during tracking but may be invoked when a measurement of a blood pressure is required. The external pressure measured by the pressure sensor may be assessed by reading a pressure value provided by a pressure sensor 102.

A device according to an embodiment of the invention for performing repeated measurements and tracking of a distinctive blood pressure level in a blood vessel in a body part comprises, a pressure control unit for controlling a pressure providing device to apply an external pressure to the body part, a detector unit for detecting appearance of a physical characteristic indicative of the distinctive blood pressure level, wherein the device is configured for controlling the pressure control unit to increase, alternatively decrease, the external pressure in a first pressure change at least until the appearance of the physical characteristic has been detected, and configured to decrease, alternatively, increase the external pressure in a second pressure change at least until the physical characteristic is not present anymore, and wherein in response to the detection of the appearance of the physical characteristic, the device is configured to measure the external pressure between the body part and the pressure providing device by use of a pressure sensor connected to the pressure providing device so as to provide a measure of the distinctive blood pressure.

The pressure sensor which may or may not be part of the blood pressure measurement device may for example be fluidly connected to the pressure providing device via a hose so that the pressure provided by the pressure providing device, e.g. an inflatable cuff, is also present in the hose. The pressure sensor may further be fluidly connected to the pressure control unit.

Advantageously, the cyclic change of the external pressures may enable fast and accurate tracking and measurement of blood pressure features.

In an embodiment the physical characteristic is a characteristic sound from the blood vessel, and the detector unit is configured for detecting the characteristic sound.

In an embodiment the physical characteristic is a particular oscillation amplitude in an oscillation in the external pressure measured by the pressure sensor, and the detector unit is configured for detecting the particular oscillation amplitude.

In an embodiment the physical characteristic is a characteristic ultrasound reflection from the blood vessel, and the detector unit is configured for detecting the characteristic ultrasound reflection.

In an embodiment the detector unit is configured for detecting a validity of the physical characteristic as a function of an amplitude, a duration or a spectral content of a signal containing the physical characteristic. Advantageously, this detection of validity may be used to filter out artefacts in the physical characteristic, e.g. characteristic sounds.

In an embodiment the device is configured for controlling the pressure control unit to change the external pressure over a pressure range, wherein the device is configured to determine a maximum oscillation amplitude present within the pressure range, and wherein the device is configured to set the particular oscillation amplitude as the maximum oscillation amplitude, and to determine a fraction of any oscillation amplitude compared to the maximum oscillation amplitude 401.

In an embodiment the device is configured to change the rate of change of the external pressure in the first and/or second pressure changes in response to a request.

In an embodiment the detector unit is configured for detecting the appearance of the physical characteristic as a function of an input signal containing information about timing of chest compressions applied to a cardiac arrest victim.

In an embodiment the detector unit is configured for detecting the appearance of the physical characteristic as a function of an input signal containing information about timing of an electrocardiogram (ECG).

A CPR device according to an embodiment of the invention configured for applying chest compressions to a cardiac arrest victim comprises the device for performing repeated measurements and tracking of a distinctive blood pressure level in a blood vessel in a body part.

In an embodiment the CPR device comprises a compression depth monitor configured to determine chest compression depth waveform or timing of chest compressions.

In an embodiment the CPR device is configured to determine a quality parameter of the performed chest compressions by use of the measured blood pressure levels.

In an embodiment the CPR device is configured to adapt chest compression as a function of the quality parameter.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for performing repeated measurements and tracking of a single distinctive blood pressure level in a blood vessel in a body part of a subject, wherein the device comprises:
   a pressure control unit for controlling a pressure providing device to apply an external pressure to the body part of the subject,
   a detector unit for detecting appearance of an oscillation amplitude in an oscillation in the external pressure measured by a pressure sensor connected to the pressure providing device so as to provide a measure indicative of the distinctive blood pressure level,
   a compression monitoring unit for generating a compression signal indicative of a timing and depth of chest compressions applied to the subject, wherein
   the device is configured to:
   (i) control the pressure control unit to change the external pressure in a first direction until a characteristic oscillation amplitude is detected, wherein the detector unit is configured to monitor for the oscillation amplitude during a change in the external pressure in the first direction;
   (ii) in response to the detection of the characteristic oscillation amplitude, measure the external pressure between the body part of the subject and the pressure providing device by use of the pressure sensor connected to the pressure providing device to provide a measure of the distinctive blood pressure level;
   (iii) in response to the detection of the characteristic oscillation amplitude, control the pressure control unit to change the external pressure in a direction opposite to the first direction, wherein the detector unit is configured to monitor for the oscillation amplitude during the change in the external pressure in the direction opposite of the first direction; and
   (iv) cyclically repeat (i), (ii) and (iii) to produce a signal that tracks the distinctive blood pressure level over time wherein the applied pressure is not reduced to atmospheric pressure between each repeat,
   wherein the distinctive blood pressure level consists of one of a diastolic blood pressure, systolic blood pressure, and mean blood pressure level,
   wherein the device is configured to control the pressure control unit to change the external pressure over a pressure range, to determine a maximum oscillation amplitude present within the pressure range, and to set the characteristic oscillation amplitude as one of the maximum oscillation amplitude or a preselected fraction of the maximum oscillation amplitude, and
   wherein the compression signal contains information about an expected timing delay of the detected appearance of the characteristic oscillation amplitude used to detect, by the detector unit, at a time delay relative to a feature in the compression signal, the appearance of the characteristic oscillation amplitude.

2. The device according to claim 1, wherein the distinctive blood pressure level is the diastolic blood pressure and wherein changing the external pressure in the first direction comprises applying the external pressure at a level which is at or near atmospheric pressure and then increasing the external pressure, and changing the external pressure in the direction opposite to the first direction comprises decreasing the external pressure.

3. The device according to claim 1, wherein the distinctive blood pressure level is the systolic blood pressure and wherein changing the external pressure in the first direction comprises applying the external pressure at a level above systole and then decreasing the external pressure, and changing the external pressure in the direction opposite to the first direction comprises increasing the external pressure.

4. An ambulatory monitoring device for monitoring the blood pressure of the subject, the ambulatory monitoring device comprising the device according to claim 1, the ambulatory monitoring device further comprising a unit arranged to be worn by the subject, the unit comprising the pressure control unit.

5. A method for tracking a diastolic blood pressure level in a blood vessel in a body part of an individual, wherein the method comprises,
   (a) applying an external pressure to the body part of the individual;
   (b) changing the external pressure applied to the body part of the individual in a first direction until a physical characteristic indicative of the diastolic blood pressure level of the individual has been detected by a detector unit, wherein the detector unit monitors for the physical characteristic during a change in the external pressure in the first direction, wherein the first direction is an increase in pressure,
   (c) in response to the detection of the physical characteristic, measuring the external pressure between the body part and a pressure providing device so as to provide a measure of the diastolic blood pressure level,
   (d) in response to the detection of the physical characteristic, changing the external pressure applied to the body part of the individual in a direction opposite to the first direction until the physical characteristic is no longer detected by the detector unit, wherein the detector unit monitors for the physical characteristic during the change in the external pressure in the direction opposite to the first direction, wherein the direction opposite to the first direction is a decrease in pressure;
   (e) cyclically repeating steps (b), (c) and (d) to produce a signal that tracks the diastolic blood pressure level over time; and
   (f) generating a compression signal indicative of a timing and depth of chest compressions applied to the individual, wherein the compression signal contains information about an expected timing of the physical characteristic used to determine, by the detector unit, at a time delay relative to a signal feature in the compression signal, the appearance and absence of the physical characteristic.

6. A device for performing repeated measurements and tracking one distinctive blood pressure level in a blood vessel in a body part during Cardiopulmonary Resuscitation of a cardiac arrest victim, the device comprising:
   a pressure source configured to apply an external pressure to the body part of the cardiac arrest victim;
   a sound detector configured to detect sound from the blood vessel;
   a pressure sensor configured to detect the one distinctive blood pressure level in the blood vessel;
   a compression monitor configured to generate a compression signal indicative of a timing and depth of chest compressions applied to the cardiac arrest victim;
   one or more computer processors configured to:
      (i) control the pressure source to change the external pressure in a first direction until the sound detector detects a characteristic sound from the blood vessel,
      (ii) in response to the sound detector detecting the characteristic sound, control the pressure sensor to measure the one distinctive blood pressure level to provide a measure of the one distinctive blood pressure level and control the pressure source to change the external pressure in a direction opposite to the first direction,
      (iii) in response to the sound detector no longer detecting the characteristic sound, returning to step (i), and
      (iv) cyclically repeat (i), (ii) and (iii) such that the pressure sensor repeatedly measures the one distinctive blood pressure level over time;
   a display configured to display the distinctive blood pressure level; and,
   a processing unit configured to generate a semi-continuous time series of values associated with the tracked distinctive blood pressure, wherein the processing unit is configured to detect return of spontaneous circulation based from the semi-continuous time series of values associated with the tracked distinctive blood pressure level,
   wherein the one distinctive blood pressure level is a single pressure level that consists of one of a diastolic blood pressure, a systolic blood pressure, and a mean blood pressure level,
   wherein the compression signal contains information about an expected timing of the characteristic sound used to determine, by the sound detector, at a time delay relative to a signal feature in the compression signal, the appearance and absence of the characteristic sound.

7. The device according to claim 6, wherein the physical characteristic comprises one of: the appearance of a characteristic sound from the blood vessel or the disappearance of a characteristic sound from the blood vessel, and wherein the detector unit is configured for detecting a characteristic sound,
   wherein the detector unit is further configured to detect validity of the characteristic sound by determining whether a sound amplitude of a measured sound is above a minimum predetermined threshold value and below a maximum predetermined threshold value.

8. The device according to claim 6, wherein the detector unit is configured to detect validity of the characteristic sound as a function of an amplitude, a duration and a spectral content of characteristic sound.

9. The device according to claim 6, wherein the distinctive blood pressure level is the diastolic blood pressure and wherein changing the external pressure in the first direction comprises applying the external pressure at a level which is at or near atmospheric pressure and then increasing the external pressure, and changing the external pressure in the direction opposite to the first direction comprises decreasing the external pressure.

10. The device according to claim 6, wherein the detector unit is configured to detect the characteristic as a function of the compression signal.

11. A Cardiopulmonary Resuscitation (CPR) device configured to determine return of spontaneous circulation in a body part of a cardiac arrest victim comprising:
- a pressure control unit for controlling a pressure providing device to apply an external pressure to the body part of the cardiac arrest victim,
- a compression monitor configured to generate a compression signal indicative of a timing and depth of chest compressions applied to the cardiac arrest victim;
- a detector unit for detecting appearance of a physical characteristic indicative of a distinctive blood pressure level, wherein
- the device is configured to:
  - (i) control the pressure control unit to change the external pressure in a first direction until the physical characteristic has been detected;
  - (ii) in response to the detection of the physical characteristic, measure the external pressure between the body part of the cardiac arrest victim and the pressure providing device by use of a pressure sensor connected to the pressure providing device so as to provide a measure of the distinctive blood pressure level;
  - (iii) in response to the detection of the physical characteristic, control the pressure control unit to change the external pressure in a direction opposite to the first direction until the physical characteristic is no longer detected; and
  - (iv) cyclically repeat (i), (ii) and (iii) to produce a signal that tracks the distinctive blood pressure level over time wherein the applied pressure is not reduced to atmospheric pressure between each repeat; and
- a processing unit configured to generate a semi-continuous time series of values associated with the tracked distinctive blood pressure level, wherein the processing unit determines return of spontaneous circulation (ROSC) based on the semi-continuous time series of values associated with the tracked distinctive blood pressure level,
- wherein the distinctive blood pressure level is one of a diastolic blood pressure or mean blood pressure level,
- wherein the compression signal contains information about an expected timing of the physical characteristic used to determine, by the detector unit, at a time delay relative to a signal feature in the compression signal, the appearance and absence of the physical characteristic.

12. The device according to claim 11, wherein the physical characteristic is a particular oscillation amplitude of an oscillation in the external pressure measured by the pressure sensor, wherein the detector unit is configured to detect oscillation amplitudes, and wherein the device is configured to control the pressure control unit to change the external pressure over a pressure range, to determine a maximum oscillation amplitude present within the pressure range, and to set the particular oscillation amplitude as the maximum oscillation amplitude or to set the particular oscillation amplitude as a particular fraction of the maximum oscillation amplitude,
- wherein the detector unit is configured to detect validity of the physical characteristic based on an amplitude, a duration and a spectral content of the detected oscillation amplitude.

13. The device according to claim 11, wherein the physical characteristic is a characteristic ultrasound reflection from the blood vessel, and wherein the detector unit is configured for detecting the ultrasound reflection,
- wherein the detector unit is configured to detect validity of the physical characteristic based on an amplitude, a duration and a spectral content of the ultrasound reflection.

14. The device according to claim 11, wherein:
- the physical characteristic is one of a characteristic amplitude of a photoplethysmograph (PPG) waveform and a characteristic morphology of the PPG waveform, and the detector unit is configured to detect the PPG waveform amplitude or PPG waveform morphology;
- wherein the detector unit is in communication with a PPG sensor and is configured to detect validity of the physical characteristic as a function of one of a PPG waveform amplitude, a PPG waveform duration and a spectral content the PPG waveform.

15. The CPR device according to claim 11, wherein the CPR device is configured to determine a quality parameter of the performed chest compressions by use of the measured distinctive blood pressure level and to adapt chest compression as a function of the quality parameter.

16. The CPR device according to claim 11, wherein the repeat of (i), (ii) and (iii) immediately follows when the physical characteristic is no longer detected in step (iii).

* * * * *